United States Patent [19]

Aumueller et al.

[11] Patent Number: 4,976,889
[45] Date of Patent: Dec. 11, 1990

[54] 4-FORMYLAMINOPIPERIDINE DERIVATIVES, THEIR USE AS STABILIZERS AND ORGANIC MATERIAL STABILIZED WITH THE SAID DERIVATIVES

[75] Inventors: Alexander Aumueller, Deidesheim; Peter Neumann, Wiesloch; Hubert Trauth, Dudenhofen, all of Fed. Rep. of Germany

[73] Assignee: BASF Aktiengesellschaft, Ludwigshafen, Fed. Rep. of Germany

[21] Appl. No.: 270,806

[22] Filed: Nov. 14, 1988

[30] Foreign Application Priority Data

Nov. 14, 1987 [DE] Fed. Rep. of Germany ....... 3738736

[51] Int. Cl.$^5$ .................. C09K 15/22; C09K 15/26; C07D 211/40; C07D 211/56
[52] U.S. Cl. .................................. 252/403; 544/129; 544/130; 546/16; 546/188; 546/190; 546/205; 546/216; 546/220; 546/221; 546/224; 546/242; 546/244; 546/275; 546/278; 546/281; 546/283; 546/284; 252/402
[58] Field of Search .............. 252/403; 544/129, 130; 546/16, 188, 190, 205, 216, 220, 221, 224, 242, 244, 275, 278, 281, 283, 284

[56] References Cited

U.S. PATENT DOCUMENTS

| 3,640,928 | 2/1972 | Murayama et al. |
| 3,684,765 | 8/1972 | Matsui et al. |
| 3,840,494 | 10/1974 | Murayama et al. |
| 3,904,581 | 9/1975 | Murayama et al. |
| 4,191,683 | 3/1980 | Brunetti et al. | 524/102 |
| 4,370,430 | 1/1983 | Hoffman | 524/103 |
| 4,459,395 | 6/1984 | Cantatore |
| 4,556,714 | 12/1985 | Karrer | 546/190 |
| 4,725,634 | 2/1988 | Ishii et al. | 524/103 |
| 4,772,708 | 9/1988 | DiBattista et al. | 546/5 |

FOREIGN PATENT DOCUMENTS 2349962 4/1974 Fed. Rep. of Germany.

Primary Examiner—Mary C. Lee
Assistant Examiner—Robert C. Whittenbaugh
Attorney, Agent, or Firm—Oblon, Spivak, McClelland, Maier & Neustadt

[57] ABSTRACT

4-Formylaminopiperidine derivatives of the formula (I)

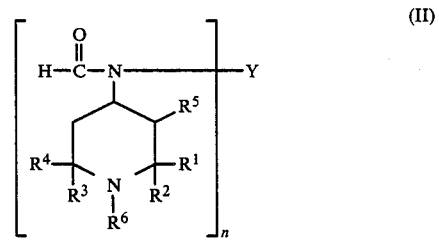

where n is 1 or 2, $R^1$ to $R^4$ are each alkyl or $R^1$ and $R^2$ or $R^3$ and $R^4$ are tetra- or pentamethylene, $R^5$ is hydrogen or alkyl, $R^6$ is hydrogen, unsubstituted or substituted alkyl, alkenyl, aralkyl or acyl, and, when n is 1, Y is hydrogen, unsubstituted or substituted alkyl, alkenyl, cycloalkyl, bicycloalkyl, aralkyl, aryl, alkyl containing heterocyclic radicals, or

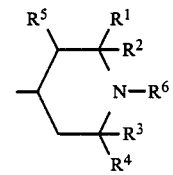

or, when n is 2, Y is alkylene, cycloalkylene, aralkylene or arylene or is alkylene which is interrupted by oxygen, nitrogen, sulfur or a 5-membered or 6-membered heterocyclic structure, and their acid addition salts have very good stabilizing properties in plastics.

15 Claims, No Drawings

4-FORMYLAMINOPIPERIDINE DERIVATIVES, THEIR USE AS STABILIZERS AND ORGANIC MATERIAL STABILIZED WITH THE SAID DERIVATIVES

It is known that 2,2,6,6-tetraalkylpiperidine derivatives are light stabilizers for organic polymers. The compatibility with polyolefins and other plastics, the duration of the protective effect, the natural color of the substances and the thermal decomposition of the stabilizers during incorporation into polymers at elevated temperatures are frequently unsatisfactory.

German Patent No. 2,349,962 describes tetraalkylpiperidine derivatives of the formula

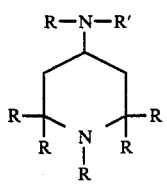

where R' is, inter atia, acyl of 2 to 18 carbon atoms. The compounds have been proposed for stabilizing polymers.

It is an object of the present invention to provide novel polyalkylpiperidine derivatives which do not have the above disadvantages.

We have found that this object is achieved with the aid of the polyalkylpiperidine compounds of the invention.

Accordingly, the present invention relates to novel 4-formylaminopiperidine derivatives of the general formula I

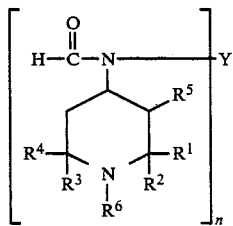

where n is 1 or 2, $R^1$, $R^2$, $R^3$ and $R^4$ independently of one another are each $C_1$–$C_4$-alkyl, or $R^1$ and $R^2$ or $R^3$ and $R^4$ together form a tetramethylene or pentamethylene group, $R^5$ is hydrogen or $C_1$–$C_4$-alkyl, $R^6$ is hydrogen, $C_1$–$C_{22}$-alkyl or $C_3$–$C_{22}$-alkenyl or is $C_7$–$C_{12}$-phenylalkyl which is unsubstituted or substituted by $C_1$–$C_4$-alkyl, fluorine, chlorine, $C_1$–$C_4$-alkoxy, methylenedioxy, ethylene-dioxy and/or di-$C_1$–$C_4$-alkylamino or is $C_1$–$C_{22}$-alkanoyl, $C_2$- or $C_3$-cyanoalkyl, $C_1$–$C_{22}$-hydroxyalkyl or $C_2$–$C_{22}$-aminoalkyl and, when n is 1, Y is hydrogen, $C_1$–$C_{22}$-alkyl, $C_3$–$C_{22}$-alkenyl, $C_3$–$C_{12}$-cycloalkyl or bicycloalkyl or is $C_2$–$C_{22}$-a-lkyl which is substituted by cyano, hydroxyl or carbo-$C_1$–$C_4$-alkoxy, or is $C_4$–$C_{22}$-alkyl which is interrupted by ether oxygen, nitrogen or sulfur, or is $C_7$–$C_{22}$-p-henyl- or diphenylalkyl which is unsubstituted or substituted by $C_1$–$C_4$-alkyl, fluorine, chlorine, $C_1$–$C_4$-a-lkoxy, methylenedioxy, ethylenedioxy or di-$C_1$–$C_4$-alkyl-amino, or is phenyl which is unsubstituted or substituted by $C_1$–$C_4$-alkyl or carbo-$C_1$–$C_4$-alkoxy, or is a radical of the formula

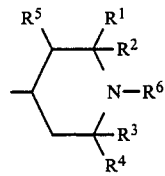

or $C_1$–$C_{22}$-alkyl containing heterocyclic radicals, or, when n is 2, Y is $C_2$–$C_{22}$-alkylene, $C_5$–$C_{22}$-cycloalkylene, $C_8$–$C_{14}$-phenylalkylene or phenylene, or is $C_4$–$C_{30}$-alkylene which is interrupted by ether oxygen, nitrogen, sulfur or a 5-membered or 6-membered heterocyclic structure, and the acid addition salts of these compounds.

The novel compounds have extremely good stabilizing properties and no natural color, are readily compatible with organic polymers, have a low vapor pressure and are stable to thermal decomposition.

$R^1$ to $R^4$ are each preferably methyl. $R^5$ is preferably hydrogen.

Specific examples of radicals $R^6$, in addition to hydrogen, are methyl, ethyl, propyl, butyl, pentyl, hexyl, benzyl, phenylethyl, phenylpropyl, methylbenzyl, allyl, acetyl, propionyl, butanoyl, pentanoyl, benzoyl, cyanomethyl, hydroxyethyl and aminoethyl.

$R^6$ is preferably methyl, acetyl, cyanomethyl, aminoethyl or, in particular, hydrogen.

Examples of Y in addition to hydrogen are:
(a) $C_1$–$C_{22}$-alkyl, such as methyl, ethyl, n-propyl, isopropyl, n-butyl, isobutyl, n-pentyl, isopentyl, hexyl, octyl, decyl, dodecyl, octadecyl, pivalyl, 3,3-dimethylbut-2-yl, neopentyl, 4-methylpent-2-yl and 2-ethylhexyl;
(b) $C_3$–$C_{22}$-alkenyl, such as allyl, butenyl, pentenyl and oleyl;
(c) $C_3$–$C_{12}$-cycloalkyl, such as cyclopropyl, cyclobutyl, cyclopentyl, cyclohexyl, methylcyclohexyl, cycloheptyl, cyclooctyl, cyclododecyl and bicycloheptyl, of which cyclopentyl and cyclohexyl are preferred;
(d) $C_2$–$C_{22}$-alkyl which is substituted by cyano, hydroxyl or carboalkoxy, such as cyanomethyl, hydroxyethyl, hydroxypropyl, hydroxybutyl, carbomethoxyethyl and carboethoxyethyl;
(e) $C_4$–$C_{22}$-alkyl which is interrupted by ether oxygen or nitrogen and is unsubstituted or substituted by hydroxyl, such as —$(CH_2)_3N(CH_3)_2$, —$(CH_2)_3N(C_2H_5)_2$, —$(CH_2)_3$—$OCH_3$, —$(CH_2)_3$—$O$—$CH(CH_3)_2$, —$(CH_2)_2O(CH_2)_2$—$OH$, —$CH_2$—$(CH_2)_2$—$CH_2$—$N(CH_2)_3$, —$(CH_2)_2$—$N[CH(CH_3)_2]_2$, —$(CH_2)_2$—$N(C_2H_5)_2$, —$(CH_2)_2N(CH_3)_2$, —$(CH_2)_2OCH_3$ and —$(CH_2)_2OCH_2CH_3$;
(f) unsubstituted or substituted $C_7$–$C_{22}$-phenyl- and diphenylalkyl, such as benzyl, methoxybenzyl, methylbenzyl, ethylbenzyl, isopropylbenzyl, trimethylbenzyl, fluorobenzyl, chlorobenzyl, methylenedioxybenzyl, phenylethyl, phenylpropyl and phenylbutyl, dimethylaminobenzyl, diphenylmethyl and 1,3-diphenylprop-2-yl;
(g) unsubstituted or substituted phenyl, such as phenyl, tolyl and carbo-$C_1$–$C_4$-alkoxy-substituted phenyl;
(h) heterocyclic radicals of the formula

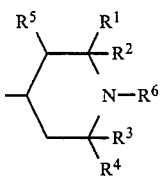

where $R^1$ to $R^6$ have the abovementioned meanings;

(i) $C_1$–$C_{22}$-alkyl containing heterocyclic structures, such as

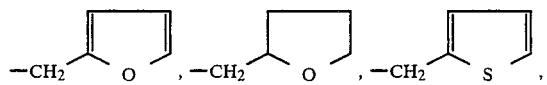

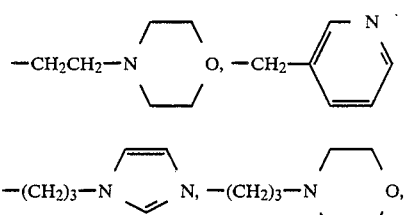

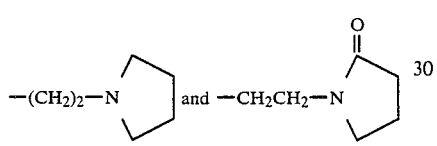

(k) $C_2$–$C_{22}$-alkylene and $C_5$–$C_{22}$-cycloalkylene, such as —(CH$_2$)$_o$—CH$_2$— (where o is from 1 to 21),

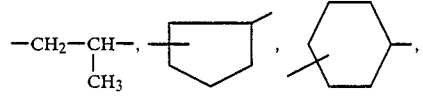

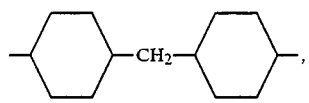

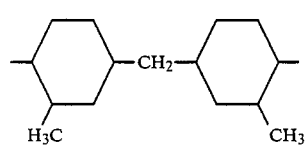

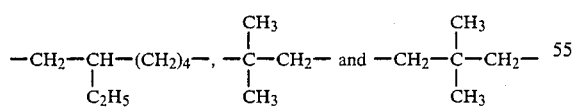

(l) $C_8$–$C_{14}$-phenylalkylene and phenylene, such as

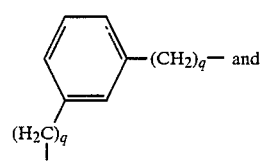

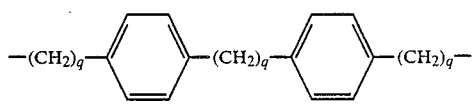

where q is 0–4;

(m) alkylene which is interrupted by ether oxygen, nitrogen, heterocyclic structures, such as

—(CH$_2$)$_3$O(CH$_2$)$_4$O(CH$_2$)$_3$—,

—(CH$_2$)$_3$O(CH$_2$)$_2$O(CH$_2$)$_2$O(CH$_2$)$_3$—

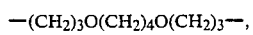

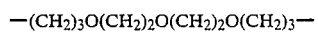

where r is from 1 to 33,

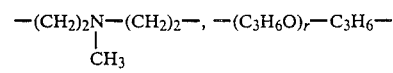

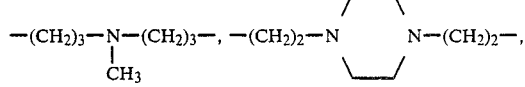

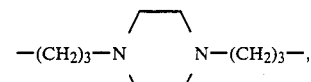

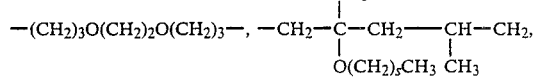

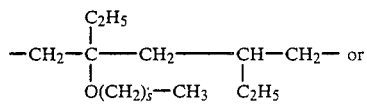

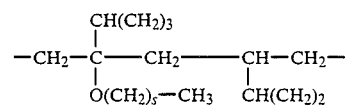

Where s is from 0 to 7.

Compounds of the general formula (I) can be prepared by reacting a compound of the general formula (II) with formic acid or a formic ester. The methyl and ethyl esters are preferred for this purpose. The reaction can be carried out in the presence or absence of a catalyst. The catalysts used may be Lewis acids, in particular titanium orthoesters and among these specifically titanium orthobutylate.

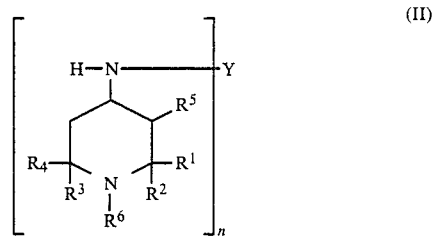

(II)

Compounds of the general formula (I) where $R^6$ is H can be converted into compounds of the general formula (I) where R is not H by a conventional method, such as alkylation, reductive amination, reaction with glycolonitrile, etc.

The novel compounds may be in the form of the free bases or of salts. Suitable anions are derived from, for example, inorganic acids and in particular from organic carboxylic acids and organic sulfonic acids.

Examples of inorganic anions are chloride, bromide, sulfate, methosulfate, tetrafluoborate, phosphate and thiocyanate.

Examples of suitable carboxylic acid anions are formate, acetate, propionate, hexanoate, cyclohexanoate, lactate, stearate, dodecylbenzoate, benzoate, acrylate, methacrylate, citrate, malonate and succinate, as well as anions of polycarboxylic acids having up to 3,000 COOH groups.

Examples of sulfonic acid anions are benzenesulfonate and tosylate.

The novel compounds are suitable for stabilizing organic material, especially plastics, against degradation by light and heat. They are also effective as metal deactivators. They are added to the plastics to be stabilized in a concentration of from 0.01 to 5, preferably from 0.02 to 1, % by weight, based on the polymer, before, during or after polymer formation.

The novel compounds can be mixed with plastics using any known apparatus and method for mixing stabilizers or other additives into polymers.

The plastics stabilized with the novel compounds can, if necessary, contain further additives, for example antioxidants, light stabilizers, metal deactivators, antistatic agents, flame-retardant agents, pigments and fillers.

Antioxidants and light stabilizers which can be added to the plastics in addition to the novel compounds are, for example, compounds based on sterically hindered phenols or are costabilizers containing sulfur or phosphorus.

Examples of such phenolic antioxidants are 2,6-di-tert-butyl-4-methylphenol, n-octadecyl $\beta$-(3,5-di-tert-butyl-4-hydroxyphenyl)-propionate, 1,1,3-tris-(2-methyl-4-hydroxy-5-tert-butylphenyl)-butane, 1,3,5-trimethyl-2,4,6-tris-(3,5-di-tert-butyl-4-hydroxybenzyl)benzene, 1,3,5-tris-(3,5-di-tert-butyl-4-hydroxybenzyl) isocyanurate, 1,3,5-tris-[$\beta$-(3,5-di-tert-butyl-4-hydroxyphenyl)-propionyloxyethyl]isocyanurate, 1,3,5-tris-(2,6-dimethyl- 3-hydroxy-4-tert-butylbenzyl) isocyanurate and pentaerythritol tetrakis-[$\beta$-(3,5-di-tert-butyl-4-hydroxyphenyl)-propionate].

Examples of suitable phosphorus-containing antioxidants are tris-(nonylphenyl) phosphite, distearyl pentaerythritol diphosphite, tris-(2,4-di-tert-butylphenyl) phosphite, tris-(2-tert-butyl-4-methylphenyl) phosphite, bis-(2,4-di-tert-butylphenyl) pentaerythritol diphosphite and tetrakis-(2,4-di-tert-butylphenyl) 4,4'-biphenylene diphosphite.

Examples of sulfur-containing antioxidants are dilauryl thiodipropionate, dimyristyl thiodipropionate, distearyl thiodipropionate, pentaerythritol tetrakis-($\beta$-laurylthiopropionate) and pentaerythritol tetrakis-($\beta$-hexylthiopropionate).

Other antioxidants and light stabilizers which can be used together with the novel compounds are, for example, 2-(2'-hydroxyphenyl)-benzotriazoles, 2-hydroxybenzophenones, aryl esters of hydroxybenzoic acids, $\alpha$-cyanocinnamic acid derivatives, nickel compounds and oxalic acid dianilides.

Examples of organic polymers which can be stabilized by the novel compounds are:

polymers of mono- and diolefins, for example low density or high density polyethylene, linear polybut-1-ene, polyisoprene, polybutadiene and copolymers of mono- or diolefins or blends of the stated polymers;

copolymers of mono- or diolefins with other vinyl monomers, such as ethylene/alkyl acrylate copolymers, ethylene/alkyl methacrylate copolymers, ethylene/vinyl acetate copolymers or ethylene acrylic acid copolymers; polystyrene;

copolymers of styrene or $\alpha$-methylstyrene with dienes or acrylyl derivatives, for example styrene/butadiene, styrene/acrylonitrile, styrene/ethyl methacrylate, styrene/butadiene/ethylacrylate and styrene/acrylonitrile/methacrylate;

ABS polymers, MBS polymers or similar polymers; halogen-containing polymers, eg. polyvinyl chloride, polyvinyl fluoride, polyvinylidene fluoride and their copolymers;

polymers derived from $\alpha,\beta$-unsaturated acids and their derivatives, such as polyacrylates, polymethacrylates, polyacrylamides and polyacrylonitriles;

polymers derived from unsaturated alcohols and amines or from their acrylyl derivatives or acetals, for example polyvinyl alcohol and polyvinyl acetate;

polyurethanes, polyamides, polyureas, polyesters, polycarbonates, polysulfones, polyethersulfones and polyether ketones.

Coatings, for example industrial coatings, can also be stabilized with the novel compounds. Among these, baking finishes are particularly noteworthy, especially automotive finishes and preferably two-coat finishes.

In this case too, the abovementioned antioxidants and light stabilizers can also be used.

The novel compounds can be added in solid or dissolved form to the coating. Its good solubility in coating systems is particularly advantageous.

The novel compounds are preferably used for stabilizing polyolefins, preferably ethylene polymers or propylene polymers, and polyurethanes.

The Examples which follow illustrate the invention.

EXAMPLE 1

78 g of 2,2,6,6-tetramethyl-4-aminopiperidine in 250 ml of ethyl formate were refluxed for 10.5 hours. The precipitate which separated out was filtered off under suction, washed with a little petroleum ether and recrystallized from toluene. 4-(Formylamino)-2,2,6,6-tetramethylpiperidine was isolated as a colorless solid of melting point 153° C.

EXAMPLE 2

56 g of 4-(N-butylamino-2,2,6,6-tetramethylpiperidine and 25 g of tetrabutyl orthotitanate in 135 ml of ethyl formate were refluxed for 4 hours.

The reaction mixture was distilled and 4-N-butyl-N-formylamino)-2,2,6,6-tetramethylpiperidine was obtained as a colorless oil of boiling point 117°-118° C./0.5 mmHg.

EXAMPLE 3

93 g of 4-(N-octylamino)-2,2,6,6-tetramethylpiperidine and 33 g of tetrabutyl orthotitanate in 175 ml of ethyl formate were refluxed for 10.5 hours. Working up as in Example 2 gave 4-(N-octyl-N-formylamino)-2,2,6,6-tetramethylpiperidine as a colorless oil of boiling point 145°-147° C./0.5 mmHg

EXAMPLE 4

81 g of 4-(N-cyclopentylamino)-2,2,6,6-tetramethylpiperidine and 34 g of tetrabutyl orthotitanate in 180 ml of ethyl formate were refluxed for 14.5 hours. After the volatile constituents had been distilled off at 70° C. and under 1 mmHg, the crystalline residue was recrystallized from petroleum ether. The colorless 4-(N-cyclopentyl-N-formylamino)-2,2,6,6-tetramethylpiperidine melts at 95° C.

EXAMPLE 5

80 g of 4-(N-cyclohexylamino)-2,2,6,6-tetramethylpiperidine and 32 g of tetrabutyl orthotitanate in 175 ml of ethyl formate were refluxed for 11 hours. Fractional distillation gave a fraction of boiling point 143°–144° C. under 0.4 mmHg. After solidification, this fraction was recrystallized from n-hexane. 4-(N-cyclohexyl-N-formylamino)-2,2,6,6-tetramethylpiperidine was isolated as a colorless solid of melting point 105° C.

EXAMPLE 6

114 g of 4-(N-phenylethylamino)-2,2,6,6-tetramethylpiperidine and 41.3 g of tetrabutyl orthotitanate in 220 ml of ethyl formate were refluxed for 14.5 hours. After the volatile constituents had been distilled off at 140° C./1 mmHg, the solidified residue was recrystallized from petroleum ether. 4-(N-phenylethyl-N-formylamino)-2,2,6,6-tetramethylpiperidine of melting point 86° C. was isolated.

EXAMPLE 7

106.5 g of 4-[N-(2,2,6,6-tetramethyl-4-piperidinylamino)]-2,2,6,6-tetramethylpiperidine and 68 g of tetrabutyl orthotitanate in 180 ml of ethyl formate were refluxed for 30 hours. The precipitate which separated out was filtered off under suction and recrystallized from methylcyclohexane. 4-[N-(2,2,6,6-tetramethyl-4-piperidinyl)-N-formylamino]-2,2,6,6-tetramethylpiperidine of melting point 188° C. was obtained.

EXAMPLE 8

10.8 g of N,N'-bis-[2,2,6,6-tetramethyl-4-piperidinyl]-ethylenediamine and 6 g of tetrabutyl orthotitanate in 70 ml of ethyl formate were refluxed for 10.5 hours. The precipitate which separated out was filtered off under suction. Recrystallization from toluene gave N,N'-bis-[2,2,6,6-tetramethyl-4-piperidinyl]-N,N'-bisformylethylenediamine (III) of melting point 210° C.

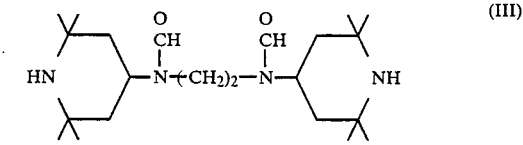

(III)

EXAMPLE 9

37 g of N,N'-bis-[2,2,6,6-tetramethyl-4-piperidinyl]-hexamethylenediamine and 3.2 g of tetrabutyl orthotitanate in 47 ml of ethyl formate were refluxed for 36 hours. The precipitate which separated out was filtered off under suction. Recrystallization from ethyl acetate gave N,N'-bis-[2,2,6,6-tetramethyl-4-piperidinyl]-N,N'-bisformylhexamethylenediamine (IV) of melting point 155° C.

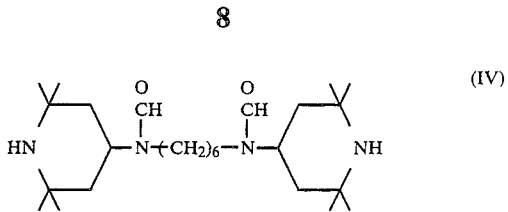

(IV)

EXAMPLE 10

(a) 155 g of 2,2,6,6-tetramethyl-4-piperidinone, 37 g of 1,3-diaminopropane and 16 g of Lewatit ® S 100 in 400 ml of isobutanol were boiled under a water separator until no further water was separated off. The catalyst was filtered off, 40 g of sodium borohydride were added to the solution, the mixture was heated at 50° C. for 4 hours and extracted by shaking with water, after which the solvent was removed under reduced pressure and the residue was subjected to fractional distillation. 64.4 g of the compound of the formula

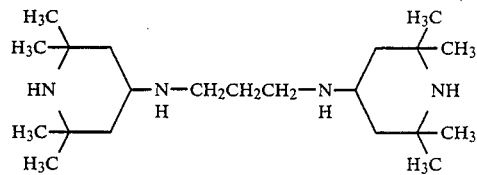

were obtained as a colorless oil of boiling point 150°–164° C./0.2 mmHg.

(b) 14.6 g of formic acid and 32.1 g of acetic anhydride were mixed, and the mixture was stirred for 20 minutes. 100 ml of toluene were added, after which a solution of 28 g of the product from Example (a) in 70 ml of toluene was added dropwise. After the mixture had stood for 16 hours at room temperature, 150 ml of water were added and the mixture was rendered alkaline with sodium hydroxide solution. The toluene phase was separated off, the aqueous phase was extracted with n-butanol, the organic phases were combined and the solvents were removed under reduced pressure from a water pump. The residue was recrystallized from methylcyclohexane.

20 g of the compound of the formula

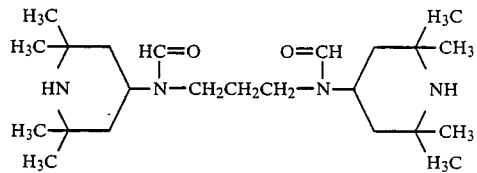

were obtained as a colorless solid of melting point 128°–129° C.

Calculated: C 67.6 H 10.8 N 13.7 O 7.8%. Found: C 67.0 H 10.8 N 13.4 O 8.6%.

EXAMPLE 11

(a) 70.2 g of 2,2,6,6-tetramethyl-4-aminopiperidine, 27.8 g of 1,4-bisbromomethylbenzene and 1 g of potassium iodide were heated at 90° C. for 0.5 hour. 250 ml of acetonitrile were added, after which the mixture was stirred for 2 hours at room temperature. The precipitate which separated out was filtered off under suction, stirred in water and rendered alkaline with sodium hydroxide solution. The mixture was extracted by shaking with n-butanol, and the solvent was removed under reduced pressure from a water pump. The residue was heated at the boil in acetonitrile, and the precipitate which separated out was filtered off under suction at room temperature.

19 g of the compound of the formula

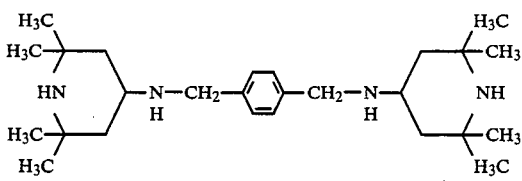

were obtained as a colorless solid of melting point 99°–100° C.

Calculated: C 75.3 H 11.2 N 13.5%. Found: C 72.8 H 10.8 N 12.8%.

(b) 8.1 g of formic acid, 17.8 g of acetic anhydride and 18.3 g of the product from (a) were reacted and worked up as in Example (10b). Recrystallization from acetonitrile gave 10 g of the compound of the formula

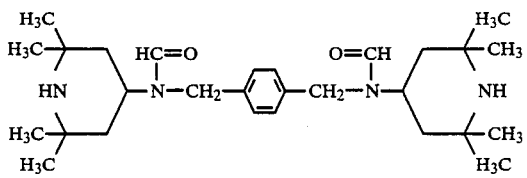

as a colorless solid of melting point 188° C.

Calculated: C 71.4 H 9.8 N 11.9 O 6.8%. Found: C 71.5 H 9.9 N 11.8 O 6.9%.

EXAMPLE 12

(a) 155 g of 2,2,6,6-tetramethylpiperidone and 87.2 g of 1-pentylamine were reacted and worked up as in Example (10a). Distillation under reduced pressure from an oil pump gave 92.1 g of the compound of the formula

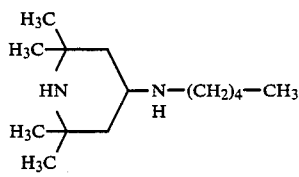

as a colorless liquid of boiling point 93° C./1 mmHg.

(b) 68 g of the product from (a) and 5.2 g of a 30% strength methanolic sodium methylate solution in 250 ml of methyl formate were refluxed for 6 hours. The excess ester was removed under reduced pressure from a water pump and the residue was distilled under reduced pressure from an oil pump. 51 g of the compound of the formula

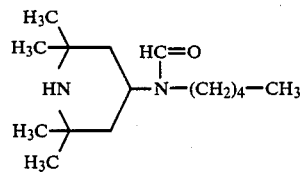

were obtained as a colorless liquid of boiling point 126°–127° C./0.3 mmHg.

Calculated: C 70.8 H 11.9 N 11.0 O 6.3%. Found: C 70.5 H 11.8 N 11.3 O 6.9%.

EXAMPLE 13

(a) 82.5 g of 1-bromohexane in 100 ml of acetonitrile were added dropwise to 78 g of 2,2,6,6-tetramethyl-4-aminopiperidine and 1 g of potassium iodide in 200 ml of acetonitrile. The mixture was stirred for 6 hours at room temperature and for 10 hours at 40°–50° C. and was filtered, the filtrate was evaporated down under reduced pressure from a water pump, the residue was dissolved in water and the solution was rendered alkaline with sodium hydroxide solution, while cooling. The mixture was extracted by shaking with n-butanol, after which the solvent was removed under reduced pressure from a water pump and the residue was distilled under reduced pressure from a water pump. 54 g of the compound of the formula

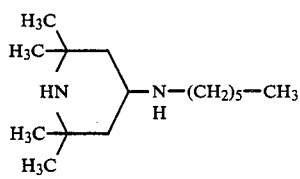

were obtained as a colorless liquid of boiling point 152°–154° C./14 mmHg.

Calculated: C 74.9 H 13.4 N 11.6%. Found: C 75.5 H 13.8 N 11.2%.

(b) 38 g of the product from a) were reacted with methyl formate and worked up as in Example (12b). 24.7 g of the compound of the formula

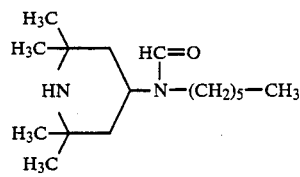

were obtained as a colorless liquid of boiling point 132° C./1 mmHg.

Calculated: C 71.6 H 12.0 N 10.4 O 5.9%. Found: C 72.3 H 12.2 N 10.5 O 5.6%.

EXAMPLE 14

(a) 156 g of decanal and 156 g of 2,2,6,6-tetramethyl-4-aminopiperidine in 500 ml of toluene were heated under a water separator until water no longer separated off. The toluene was removed under reduced pressure from a water pump, 600 ml of methanol and 40 g of sodium borohydride were added to the residue and the mixture was heated at 50° C. for 4 hours. The methanol was distilled off and the residue was extracted by shaking with ethyl acetate and water. After phase separation and drying of the ethyl acetate phase, the solvent was removed under reduced pressure from a water pump and the residue was distilled under reduced pressure from an oil pump. 46.3 g of the compound of the formula

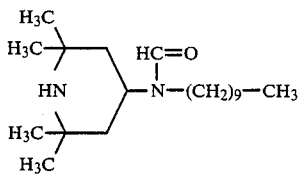

were obtained as a yellowish liquid of boiling point 144°–146° C./0.1 mmHg.

(b) 13.8 g of formic acid and 30 g of acetic anhydride were stirred for 0.5 hour. 150 ml of dichloromethane were added, after which 45 g of the product from (a) in 100 ml of dichloromethane wree added dropwise. The mixture was stirred for 5 hours at room temperature, after which 250 ml of ice water were added, the mixture was rendered alkaline with sodium hydroxide solution and, after phase separation, the organic phase was distilled under reduced pressure from a water pump. 25 g of the compound of the formula

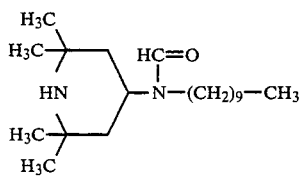

were obtained as a colorless liquid of boiling point 176°–178° C./0.1 mmHg.

Calculated: C 74.0 H 12.4 N 8.6 O 4.9%. Found: C 73.8 H 12.4 N 8.8 O 5.4%

EXAMPLE 15

(a) 155 g of 2,2,6,6-tetramethyl-4-piperidone and 185 g of 1-amionododecane were reacted and worked up as in Example (10a). 84.9 g of the compound of the formula

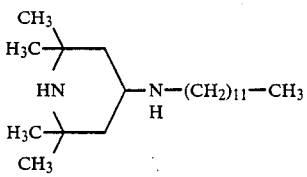

were obtained as a yellowish liquid of boiling point 120°–126° C.

(b) 35.6 g of the product from (a) were reacted as in Example (12b). The volatile constituents were distilled off at up to 190° C. under 0.4 mmHg. The residue consisted of 33.3 g of the compound of the formula

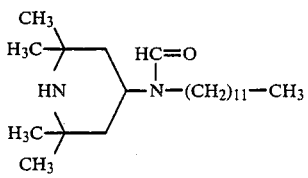

Calculated: C 74.9 H 12.6 N 7.9 O 4.5%. Found: C 75.4 H 12.9 N 5.8 O 6.1%.

EXAMPLE 16

(a) 155 g of 2,2,6,6-tetramethyl-4-piperidone and 269.5 g of 1-aminooctadecane were reacted and worked up as in Example (10a).

4.2 g of the compound of the formula

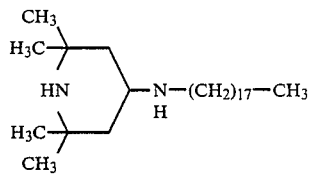

were obtained as a colorless oil of boiling point 176°–180° C./0.3 mmHg.

(b) 40 g of the product from (a) were reacted and worked up as in Example (12b). The residue which remained after the ethyl acetate had been removed was recrystallized from acetonitrile. 19 g of the compound of the

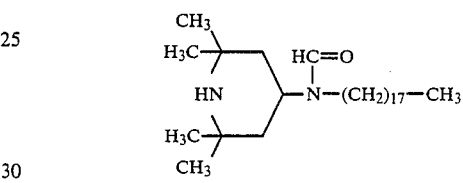

were obtained as a colorless solid of melting point 60° C.

Calculated: C 77.0 H 12.9 N 6.4 O 3.7%. Found: C 76.7 H 12.9 N 6.3 O 3.9%.

EXAMPLE 17

(a) 156 g of 2,2,6,6-tetramethyl-4-aminopiperidine, g of acetone and 5 g of p-toluenesulfonic acid monohydrate in 300 ml of toluene were boiled under a water separator. A further 29 g of acetone were added after 4.5 hours, 29 g of acetone after 7 hours, 87 g of acetone and 5 g of p-toluenesulfonic acid monohydrate after 11 hours, 30 g of acetone after 13.5 hours and a further 30 g of acetone after 20 hours. After a further 2 hours, the solvent was removed under reduced pressure from a water pump, 250 ml of methanol and 38 g of sodium borohydride were added to the residue and the mixture was boiled for 2 hours. Thereafter, it was diluted with 400 ml of water and extracted with dichloromethane. After phase separation and drying of the organic phase over magnesium sulfate, the solvent was removed under reduced pressure from a water pump and the residue was subjected to fractional distillation. 58 g of the compound of the formula

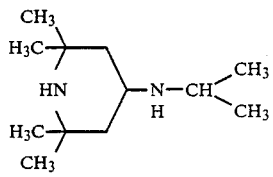

were obtained as a colorless liquid of boiling point 100°–102° C./24 mmHg.

(b) 55 g of the product from (a) were reacted and worked up as in Example (14b). The organic phase was evaporated down, after which the residue was recrystallized from acetonitrile. 21 g of the compound of the formula

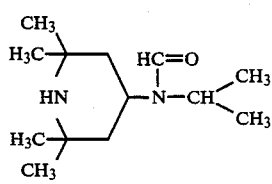

were obtained as a colorless solid of melting point 142° C.

Calculated: C 69.0 H 11.6 N 12.4 O 7.1%. Found: C 68.8 H 11.5 N 12.5 O 6.6%.

EXAMPLE 18

(a) 108 g of isobutyraldehyde and 257 g of 2,2,6,6-tetramethyl-4-aminopiperidine were reacted and worked up as in Example (14a). 218 g of the compound of the formula

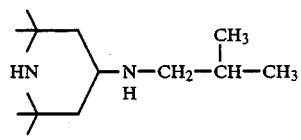

were obtained as a colorless liquid of boiling point 122° C./28 mmHg

Calculated: C 73.5 H 13.3 N 13.2%. Found: C 73.2 H 13.1 N 13.4%.

(b) 63.6 g of the product from (a) were reacted and worked up as in Example (14b). 50 g of the compound of the formula

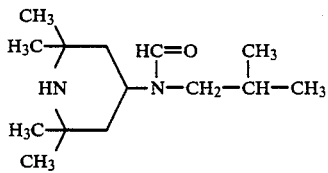

were obtained as a colorless oil of boiling point 136° C./2.5 mmHg.

After the oil had been allowed to stand, it solidified to give a colorless solid of melting point 36° C.

Calculated: C 69.9 H 11.7 N 11.6 O 6.6%. Found: C 69.8 H 11.4 N 11.9 O 7.5%.

EXAMPLE 19

(a) 151 g of 1-bromo-3-methylbutane in 100 ml of acetonitrile were added dropwise to a mixture of 156 g of 2,2,6,6-tetramethyl-4-aminopiperidine, 101 g of triethylamine, 1 g of potassium iodide and 150 ml of acetonitrile, and the mixture was stirred for 5 hours at room temperature and refluxed for 4 hours while stirring.

The solvent was removed under reduced pressure from a water pump, the residue was dissolved in water and the solution was rendered alkaline with sodium hydroxide solution. The solution was extracted by shaking with n-butanol and, after phase separation, the organic phase was subjected to fractional distillation under reduced pressure from a water pump. 95 g of the compound of the formula

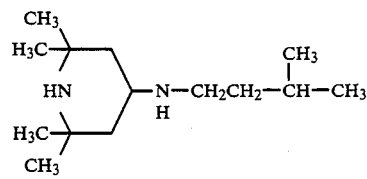

were obtained as a colorless liquid of boiling point 125°–126° C./12 mmHg.

Calculated: C 74.3 H 13.3 N 12.2%. Found: C 74.1 H 13.2 N 12.6%.

(b) 53 g of the product from (a) were reacted and worked up as in Example (12b). 45 g of the compound of the formula

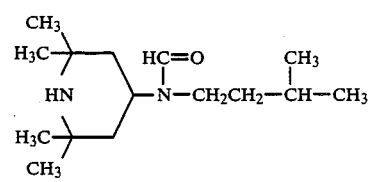

were obtained as a colorless oil of boiling point 120°–121° C./0.3 mmHg.

Calculated: C 70.8 H 11.9 N 11.0 O 6.3%. Found: C 70.8 H 11.5 N 10.9 O 6.5%.

EXAMPLE 20

(a) 125 g of 3,3-dimethyl-2-butanone, 203 g of 2,2,6,6-tetramethyl-4-aminopiperidine and 5 g of p-toluenesulfonic acid monohydrate were boiled under a water separator until the water no longer separated off. The solvent was removed under reduced pressure from a water pump, 300 ml of methanol and 47.5 g of sodium borohydride were added to the residue and the mixture was refluxed for 4 hours. It was diluted with 400 ml of ice water and extracted with dichloromethane, and, after phase separation, the organic phase was evaporated down. The residue was subjected to fractional distillatin. 164 g of the compound of the formula

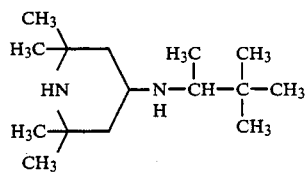

were obtained as a colorless liquid of boiling point 84°–86° C./0.5 mmHg.

Calculated: C 74.9 H 13.4 N 11.6%. Found: C 74.3 H 13.2 N 12.5%.

(b) 60 g of the product from (a) were reacted and worked up as in Example (14b). 44 g of the compound of the formula

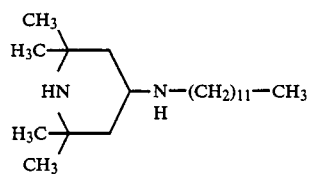

were obtained as a colorless liquid of boiling point 23° C./0.3 mmHg.

Calculated: C 71.6 H 12.0 N 10.4 O 6.0%. Found: C 71.5 H 11.8 N 10.6 O 6.7%.

EXAMPLE 21

(a) 125 g of 4-methyl-2-pentanone, 202 g of 2,2,6,6-tetramethyl-4-aminopiperidine and 5 g of p-toluenesulfonic acid monohydrate were reacted and worked up as in Example (20a). 203 g of the compound of the formula

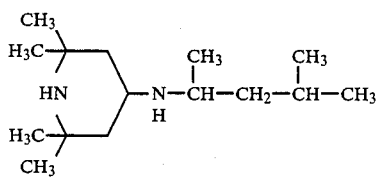

were obtained as a colorless liquid of boiling point 130°–131° C./21 mmHg.

Calculated: C 74.9 H 13.4 N 11.7%. Found: C 74.5 H 13.4 N 12.1%.

(b) 60 g of the product from (a) were reacted and worked up as in Example (14b). 45 g of the compound of the formula

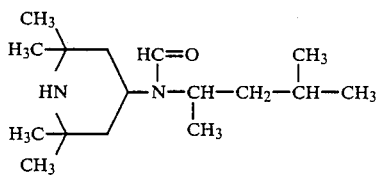

were obtained as a colorless liquid of boiling point 120° C./0.3 mmHg.

Calculated: C 71.6 H 12.0 N 10.4 O 6.0%. Found: C 70.9 H 11.9 N 10.8 O 6.7%.

EXAMPLE 22

(a) 96.5 g of 1-bromo-2-ethylhexane in 100 ml of acetonitrile were added dropwise to 78 g of 2,2,6,6-tetramethyl-4-aminopiperidine and 1 g of potassium iodide in 200 ml of acetonitrile. After the mixture had been stirred for 4.5 hours at room temperature and for 8 hours at 50° C., a further 78 g of 2,2,6,6-tetramethyl-4-aminopiperidine were added dropwise and the stirred mixture was kept at 50° C. for 2 hours.

The mixture was cooled and then filtered, the filtrate was freed from the solvent and the residue thus obtained was dissolved in water and the solution rendered alkaline in sodium hydroxide solution. After extraction by shaking with n-butanol and phase separation, the nbutanol was removed under reduced pressure from a water pump and the residue was subjected to fractional distillation under reduced pressure from an oil pump. 51.3 g of the compound of the formula

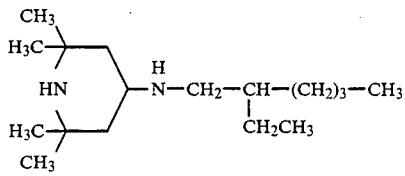

were obtained as a colorless liquid of boiling point 124° C./1.5 mmHg.

Calculated: C 76.0 H 13.5 N 10.4%. Found: C 75.5 H 13.3 N 10.6%.

(b) 37 g of the product from (a) were reacted (reaction time 11 hours) and worked up as in Example (12b). 26 g of the compound of the formula

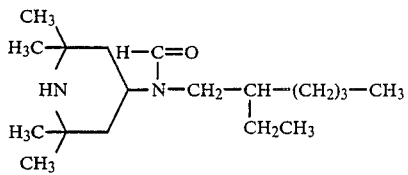

were obtained as a colorless liquid of boiling point 156° C./1 mmHg.

Calculated: C 72.9 H 12.2 N 9.4 O 5.4%. Found: C 72.9 H 12.0 N 9.8 O 5.6%.

EXAMPLE 23

(a) 89 g of 4-methylcyclohexanone, 129 g of 2,2,6,6-tetramethylpiperidine and 5 g of p-toluenesulfonic acid monohydrate were reacted and worked up as in Example (20a). 76 g of the compound of the formula

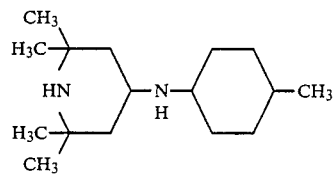

were obtained as a colorless liquid of boiling point 174°–176° C./20 mmHg.

Calculated: C 76.1 H 12.8 N 11.1%. Found: C 76.7 H 12.6 N 10.8%.

(b) 45 g of the product from (a) were reacted and worked up as in Example (14b). After removal of the solvent, the residue was recrystallized from n-hexane. 14 g of the compound of the formula

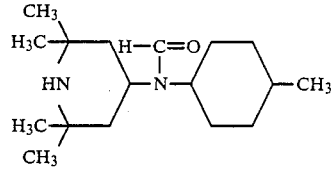

were obtained as a colorless solid of melting point

Calculated: C 72.8 H 11.5 N 10.0 O 5.7%. Found: C 72.9 H 11.6 N 9.8 O 5.8%.

EXAMPLE 24

2 g of benzophenone, 171.6 g of 2,2,6,6-tetramethyl-4-aminopiperidine and 5 g of p-toluenesulfonic acid monohydrate in 350 ml of xylene were boiled under a water separator until no more water separated off. The mixture was cooled and then evaporated down and ml of methanol and 19 g of sodium borohydride were added. After the mixture had been refluxed for 2.5 hours, a further 19 g of sodium borohydride were introduced and boiling was continued for a further 5 hours. The mixture was discharged into 2 l of water and the precipitate which separated out was filtered off under d recrystallized from isopropanol. 133 g of the compound of the formula

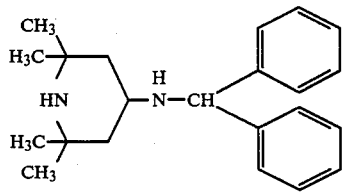

were obtained as a colorless solid of melting point 86° C.

Calculated: C 81.9 H 9.4 N 8.7%. Found: C 81.8 H 9.5 N 8.7%.

(b) 50 g of the product from (a) were reacted and worked up as in Example (14b). After removal of the solvent, the residue was recrystallized from n-hexane. 32.7 g of the compound of the formula

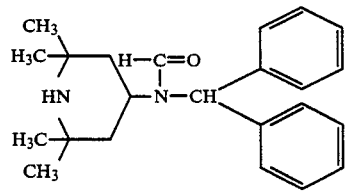

were obtained as a colorless solid of melting point 86° C.

Calculated: C 78.8 H 8.6 N 8.0 O 4.6%. Found: C 77.8 H 8.6 N 8.0 O 5.0%.

EXAMPLE 25

(a) 126 g of 1,3-diphenylacetone, 103 g of 2,2,6,6-tetramethyl-4-aminopiperidine and 5 g of p-toluenesulfonic acid monohydrate in 350 ml of xylene were boiled under a water separator until water no longer separated off. After the xylene had been distilled off, the residue was taken up in 250 ml of methanol, 23 g of sodium borohydride were added and the mixture was refluxed for 4 hours.

400 ml of water were added, after which the mixture was extracted with dichloromethane and, after phase separation, the organic solvent was removed under reduced pressure from a water pump, and the residue thus obtained was distilled under reduced pressure from an oil pump. 147 g of the compound of the formula

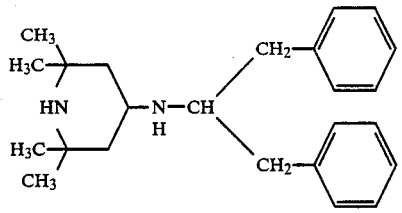

were obtained as a colorless oil of boiling point 179° C./0.1 mmHg.

Calculated: C 82.2 H 9.8 N 8.0%. Found: C 82.1 H 9.9 N 8.0%.

(b) 52.5 g of the product from (a) were reacted and worked up as in Example (14b). After removal of the solvent, the residue obtained was recrystallized from acetonitrile. 43 g of the compound of the formula

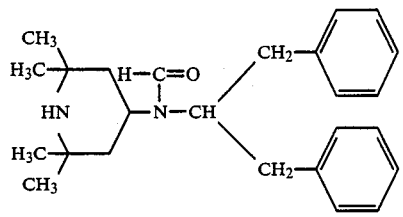

were obtained as a colorless solid of melting point 158° C.

Calculated: C 79.3 H 9.0 N 7.4 O 4.2%. Found: C 79.2 H 9.1 N 7.4 O 4.4%.

EXAMPLE 26

(a) 78.6 g of benzyl methyl ketone and 91.4 g of 2,2,6,6-tetramethyl-4-aminopiperidine were reacted and worked up similarly to Example (10a). 43.7 g of the compound of the formula

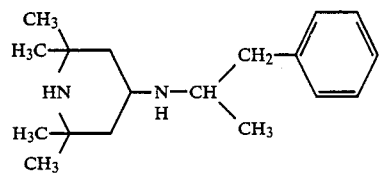

were obtained as a colorless oil of boiling point 125° C./0.3 mmHg.

Calculated: C 78.8 H 11.0 N 10.2%. Found: C 78.4 H 10.9 N 10.5%.

(b) 24 g of the product from (a) were reacted and worked up as in Example (14b). After removal of the solvent, the residue obtained was recrystallized from methyl tert-butyl ether. 9 g of the compound of the formula

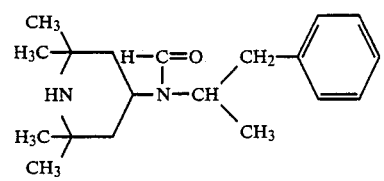

were obtained as a colorless solid of melting point 102° C.

Calculated: C 75.4 H 10.0 N 9.3 O 5.3%. Found: C 75.4 H 10.0 N 9.2 O 5.3%.

EXAMPLE 27

(a) 107 g of benzylamine and 155 g of 2,2,6,6-tetramethyl-4-piperidone were boiled with 16 g of Lewatitt ® S in 400 ml of toluene under a water separator until water no longer separated off. Further reaction and working up were carried out as in Example (10a). 119 g of the compound of the formula

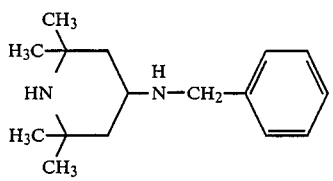

were obtained as a colorless liquid of boiling point 124° C./0.5 mmHg.

(b) 50 g of the product from (a) were reacted and worked up similarly to Example (12b). After removal of the ethyl acetate, the residue was recrystallized from methylcyclohexane. 41 g of the compound of the formula

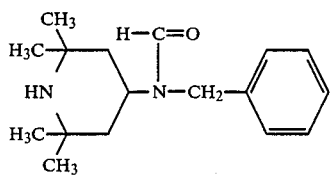

were obtained as a colorless solid of melting point 106° C.

Calculated: C 72.0 H 9.6 N 9.9 O 8.5%. Found: C 72.3 H 9.2 N 9.7 O 8.2%.

The compound crystallized with 0.5 mole of water of crystallization.

EXAMPLE 28

(a) 102 g of 4-methylbenzaldehyde and 140.4 g of 2,2,6,6-tetramethyl-4-aminopiperidine in xylene were reacted, without a catalyst, and worked up similarly to Example (25a). Distillation gave 170 g of the compound of the formula

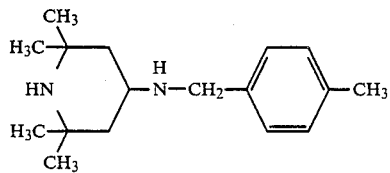

as a colorless liquid of boiling point 138° C./0.5 mmHg.

Calculated: C 78.4 H 10.8 N 10.7%. Found: C 78.1 H 10.9 N 11.2%.

(b) 52 g of the product from (a) were reacted and worked up as in Example (14b). After removal of the solvent, the residue was recrystallized from acetonitrile. 39 g of the compound of the formula

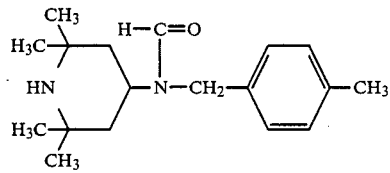

were obtained as a colorless solid of melting point 119° C.

Calculated: C 75.0 H 9.8 N 9.7 O 5.5%. Found: C 75.1 H 9.8 N 9.7 O 5.6%.

EXAMPLE 29

(a) 136 g of 4-methoxybenzaldehyde and 172 g of 2,2,6,6-tetramethyl-4-aminopiperidine were reacted and worked up as in Example (28a). 190 g of the compound of the formula

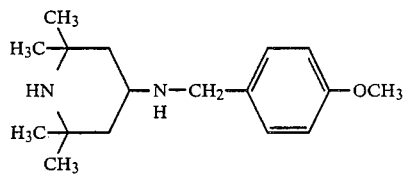

were obtained as a colorless liquid of boiling point 150°–152° C./0.3 mmHg.

Calculated: C 73.9 H 10.2 N 10.1 O 5.8%. Found: C 73.1 H 10.2 N 10.7 O 6.2%.

(b) 55 g of the product from (a) were reacted and worked up as in Example (14b). After removal of the solvent, the residue was recrystallized from methyl tertbutyl ether. 42 g of the compound of the formula

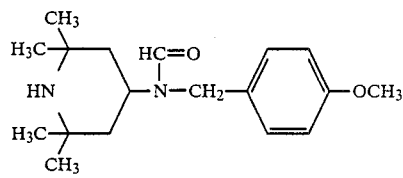

were obtained as a colorless solid of melting point 108° C.

Calculated: C 71.0 H 9.3 N 9.2 O 10.5%. Found: C 70.9 H 9.4 N 9.2 O 10.6%.

EXAMPLE 30

(a) 100 g of 4-dimethylaminobenzaldehyde and 109 g of 2,2,6,6-tetramethyl-4-aminopiperidine were reacted and worked up as in Example (28a). 142 g of the compound of the formula

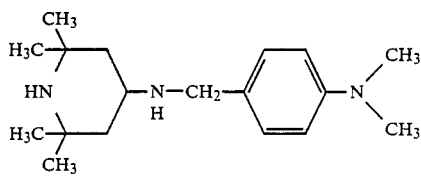

were obtained as a colorless oil of boiling point 162° C./0.1 mmHg which, after it had been allowed to stand, solidified to a colorless solid of melting point Calculated: C 74.7 H 10.8 N 14.5%. Found: C 74.7 H 10.8 N 14.8%.

(b) 57.8 g of the product from (a) were reacted and worked up as in Example (14b). After removal of the solvent, the residue was recrystallized from acetonitrile. 37 g of the compound of the formula

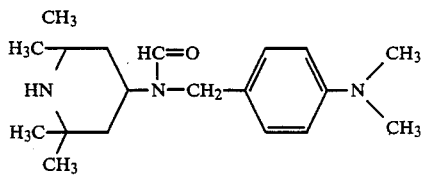

were obtained as a colorless solid of melting point 126° C.

Calculated: C 71.9 H 9.8 N 13.2 O 5.0%. Found: C 72.0 H 10.0 N 13.3 O 5.1%.

EXAMPLE 31

(a) 101 g of 4-fluorobenzaldehyde and 128 g of 2,2,6,6-tetramethyl-4-aminopiperidine were reacted and worked up as in Example (28a). 161 g of the compound of the formula

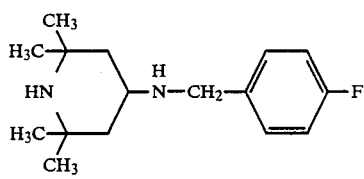

were obtained as a colorless liquid of boiling point 120°–122° C./0.2 mmHg.

Calculated: C 72.7 H 9.5 F 7.2 N 10.6%. Found: C 72.6 H 9.6 F 7.4 N 10.9%.

(b) 53 g of the product from (a) were reacted and worked up as in Example (14b). After removal of the solvent, the residue was recrystallized from acetonitrile. 25 g of the compound of the formula

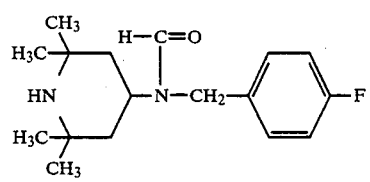

were obtained as a colorless solid of melting point 108° C.

Calculated: C 69.8 H 8.6 F 6.5 N 9.6%. Found: C 69.8 H 8.7 F 6.4 N 9.6%.

EXAMPLE 32

(a) A solution of 161 g of 4-chlorobenzyl chloride in 100 ml of acetonitrile was added dropwise to 156 g of 2,2,6,6-tetramethyl-4-aminopiperidine, 101 g of triethylamine and 1 g of potassium iodide in 100 ml of acetonitrile. The mixture was stirred for 14 hours at room temperature, refluxed for 1 hour and cooled, after which the precipitate which separated out was filtered off under suction, stirred with 1 l of water and rendered alkaline with sodium hydroxide solution and the product was again filtered off under suction, washed with water and recrystallized from acetonitrile. 127 g of the compound of the formula

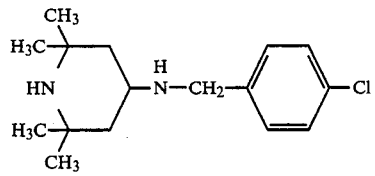

were obtained as a colorless solid of melting point 61° C.

Calculated: C 68.4 H 9.0 Cl 12.6 N 10.0%. Found: C 68.4 H 9.1 Cl 12.7 N 9.9%.

(b) 50 g of the product from (a) in toluene were reacted similarly to Example (14b). After removal of the solvent, the residue was recrystallized from methyl tert-butyl ether. 34 g of the compound of the formula

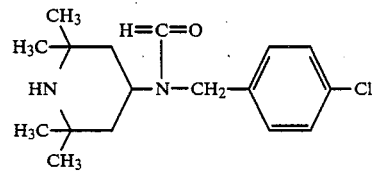

were obtained as a colorless solid of melting point 121° C.

Calculated: C 66.1 H 8.1 Cl 11.5 N 9.1 O 5.2%. Found: C 66.2 H 8.3 Cl 11.4 N 9.1 O 5.3%.

EXAMPLE 33

(a) 107 g of pyridine-3-carbaldehyde and 172 g of 2,2,6,6-tetramethyl-4-aminopiperidine were reacted and worked up similarly to Example (28a). 157 g of the compound of the formula

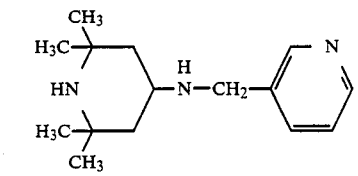

were obtained as a colorless oil of boiling point 140° C./0.2 mmHg.

Calculated: C 72.8 H 10.2 N 17.0%. Found: C 72.1 H 10.3 N 17.0%.

(b) 49.4 g of the product from (a) were reacted and worked up as in Example (14b). After removal of the solvent, the residue was recrystallized from acetonitrile. 28 g of the compound of the formula

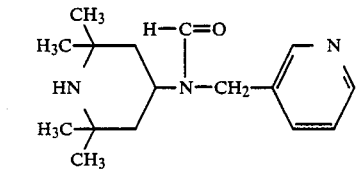

were obtained as a colorless solid of melting point

Calculated: C 69.8 H 9.1 N 15.2 O 5.8%. Found: C 69.8 H 9.2 N 15.3 O 6.0%.

EXAMPLE 34

(a) 310 g of 2,2,6,6-tetramethyl-4-piperidine and 178 g of 2-ethoxyethylamine were reacted and worked up as in Example (10a). 8.4 g of the compound of the formula

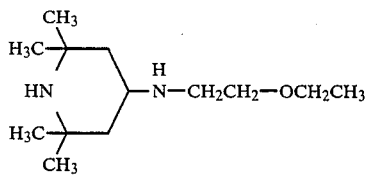

were obtained as a colorless liquid of boiling point 84° C./2 mmHg.

Calculated: C 68.4 H 12.4 N 12.3 O 7.0%. Found: C 67.3 H 12.4 N 12.2 O 7.7%.

(b) 45 g of the product from (a) were reacted and worked up as in Example (12b). 31.5 g of the compound of the formula

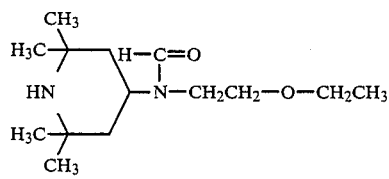

were obtained as a colorless liquid of boiling point 118° C./0.2 mmHg.

Calculated: C 65.6 H 11.0 N 10.9 O 12.5%. Found: C 65.2 H 11.2 N 11.1 O 13.0%.

EXAMPLE 35

(a) 89 g of 3-ethoxypropylamine and 155 g of 2,2,6,6-tetramethyl-4-piperidone were reacted and worked up as in Example (10a). 61.3 g of the compound of the formula

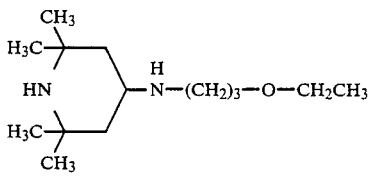

were obtained as a colorless liqiud of boiling point 108°–110° C./1.5 mmHg.

(b) 34.5 g of the product from (a) were reacted and worked up as in Example (12b). 17 g of the compound of the formula

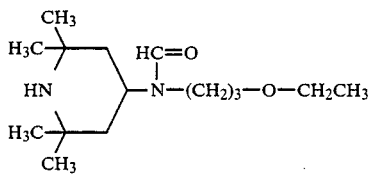

were obtained as a colorless liquid of boiling point 128° C./0.1 mmHg.

Calculated: C 66.6 H 11.2 N 10.3 O 11.8%. Found: C 66.2 H 11.1 N 10.6 O 12.4%.

EXAMPLE 36

(a) 187 g of 3-(2-ethylhexyloxy)-propylamine and 155 g of 2,2,6,6-tetramethyl-4-piperidone were reacted and worked up as in Example 10a.

191 g of the compound of the formula

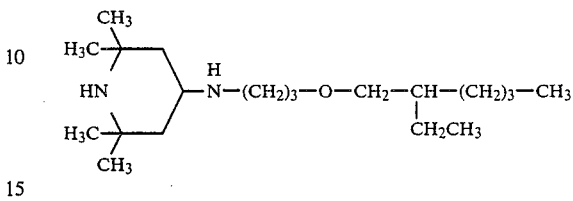

were obtained as a colorless oil of boiling point 122° C./1.5 mmHg.

Calculated: C 73.6 H 13.0 N 8.6 O 4.9%. Found: C 73.1 H 12.9 N 8.8 O 5.6%.

(b) 32.6 g of the product from (a) were reacted and worked up as in Example (14b). 23 g of the compound of the formula

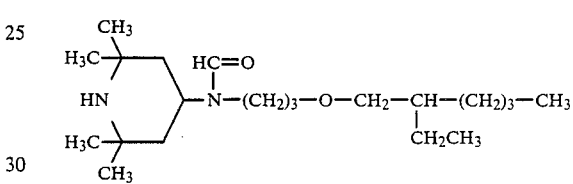

were obtained as a yellowish liquid of boiling point 172°–174° C./0.25 mmHg.

Calculated: C 71.1 H 11.9 N 7.9 O 9.0%. Found: C 70.8 H 11.8 N 8.0 O 9.9%.

EXAMPLE 37

(a) 102 g of 3-dimethylaminopropylamine and 155 g of 2,2,6,6-tetramethyl-4-piperidone were reacted and worked up as in Example (10a). 49.5 g of the compound of the formula

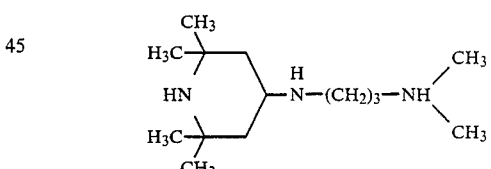

were obtained as a colorless liquid of boiling point 88°–92° C./0.15 mmHg.

(b) 47 g of the product from (a) were reacted and worked up as in Example (12b). 15 g of the compound of the formula

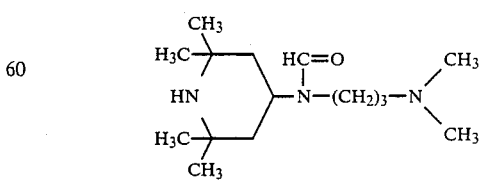

were obtained as a colorless oil of boiling point 138° C./0.2 mmHg, which, after being allowed to stand, solidified to a colorless solid of melting point 62° C.

Calculated: C 66.9 H 11.6 N 15.6 O 5.9%. Found: C 67.0 H 11.5 N 15.4 O 6.2%.

EXAMPLE 38

(a) 232 g of 2-diethylaminoethylamine and 310 g of 2,2,6,6-tetramethyl-4-piperidone were reacted and worked up as in Example (10a). 185 g of the compound of the formula

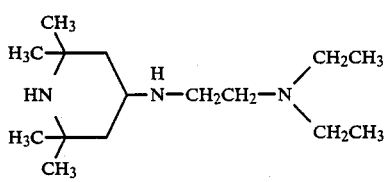

were obtained as a colorless liquid of boiling point 98°-100° C./0.3 mmHg.

(b) 50.8 g of the product from (a) were reacted and worked up as in Example (12b). 28.7 g of the compound of the formula

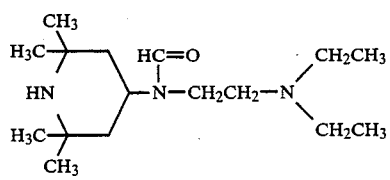

were obtained as a colorless liquid of boiling point 147° C./0.15 mmHg.

Calculated: C 67.8 H 11.7 N 14.8 O 5.7%. Found: C 67.2 H 11.7 N 15.2 O 6.5%.

EXAMPLE 39

(a) 288.4 g of 2-(diisopropylamino)-ethylamine and 310 g of 2,2,6,6-tetramethyl-4-piperidone were reacted and worked up as in Example (10a). 177.6 g of the compound of the formula

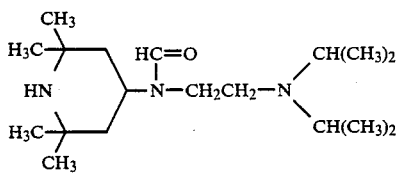

were obtained as a colorless liquid of boiling point 108°-110° C./0.35 mmHg.

Calculated: C 72.0 H 13.2 N 14.8%. Found: C 71.8 H 13.1 N 15.0%.

(b) 60 g of the product from (a) were reacted and worked up as in Example (12b). 44.4 g of the compound of the formula

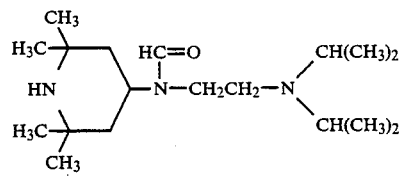

were obtained as a colorless oil of boiling point 133°-134° C./0.1 mmHg, which solidified to a colorless solid of melting point 69° C.

Calculated: C 69.4 H 12.0 N 13.5 O 5.3%. Found: C 69.7 H 11.9 N 13.7 O 5.3%.

EXAMPLE 40

(a) 228.4 g of 2-(1-pyrrolidyl)-ethylamine and 310 g of 2,2,6,6-tetramethyl-4-piperidone were reacted and worked up as in Example (10a). 182 g of the compound of the formula

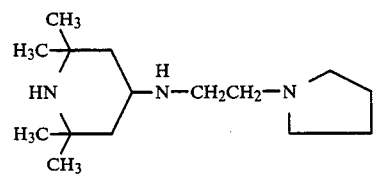

were obtained as a colorless liquid of boiling point 117°-121° C./0.1 mmHg.

Calculated: C 71.1 H 12.3 N 16.6%. Found: C 70.8 H 12.4 N 16.5%.

(b) 50 g of the product from (a) were reacted and worked up as in Example (12b). 34 g of the compound of the formula

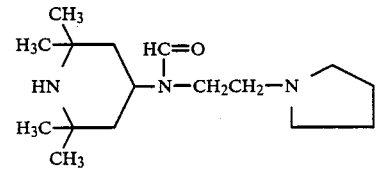

were obtained as a colorless oil of boiling point 143° C./0.1 mmHg, which solidified to a colorless solid of melting point 77° C.

Calculated: C 68.3 H 11.1 N 14.9 O 5.7%. Found: C 68.4 H 11.3 N 15.0 O 5.8%.

EXAMPLE 41

(a) 122 g of bicyclo[2.2.1]heptan-2-one, 163.8 g of 2,2,6,6-tetramethyl-4-aminopiperidine and 5 g of p-toluenesulfonic acid monohydrate in 400 ml of xylene were heated under a water separator until no more water separated off. The mixture was cooled and then filtered and the filtrate was freed from the solvent under reduced pressure from a water pump. After cooling, the residue solidified. It consisted of 242 g of the compound of the formula

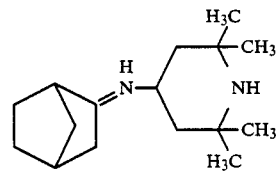

in the form of a colorless solid of melting point 61°-62° C.

Calculated: C 77.4 H 11.3 N 11.3%. Found: C 76.9 H 11.3 N 11.1%.

(b) 100 g of the product from (a) in 400 ml of toluene were hydrogenated with 10 g of Raney nickel under 300 bar of hydrogen and at 100° C. until hydrogen was no longer absorbed. After the mixture had been filtered, the solvent was removed under reduced pressure from a water pump and the residue was subjected to fractional distillation under reduced pressure from an oil pump. 71 g of the compound of the formula

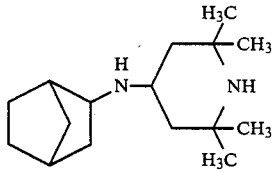

were obtained as a colorless oil of boiling point 99°–100° C./0.1 mmHg, which solidified to a colorless solid of melting point 36° C.

Calculated: C 76.7 H 12.1 N 11.2%. Found: C 76.7 H 12.2 N 11.4%.

(c) 34.5 g of formic acid and 76.5 g of acetic anhydride were stirred for 0.5 hour. Thereafter, 40 g of the product from (b) were introduced. After the mixture had been left to stand overnight, 450 ml of ice water were added and the mixture was rendered alkaline with sodium hydroxide solution and extracted by shaking with dichloromethane. After drying over magnesium sulfate, the organic phase was freed from the solvent and the residue was recrystallized from acetonitrile. 19 g of the compound of the formula

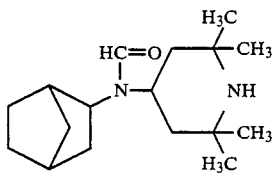

were obtained as a colorless solid of melting point 92° C.

Calculated: C 73.3 H 10.9 N 10.1 O 5.7%. Found: C 73.2 H 10.9 N 10.1 O 5.8%.

EXAMPLE 42

(a) 118.4 g of 4-isopropylbenzaldehyde and 132.6 g of 2,2,6,6-tetramethyl-4-aminopiperidine were reacted and worked up as in Example (28a). 165 g of the compound of the formula

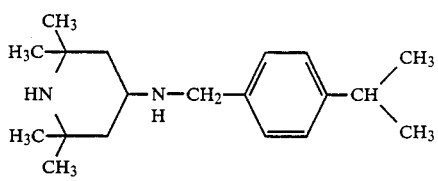

were obtained as a colorless liquid of boiling point 144°–145° C./0.1 mmHg.

Calculated: C 79.1 H 11.2 N 9.7%. Found: C 78.7 H 11.2 N 10.0%.

(b) 72 g of the product from (a) were reacted and worked up as in Example (14b). Recrystallization from acetonitrile gave 50 g of the compound of the formula

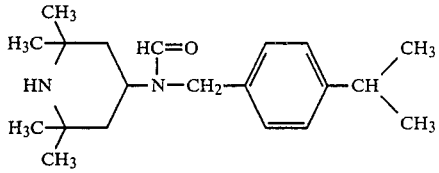

as a colorless solid of melting point 105° C.

Calculated: C 75.9 H 10.2 N 8.8 O 5.0%. Found: C 75.7 H 10.2 N 8.8 O 5.5%.

EXAMPLE 43

(a) 112.5 g of 3,4-(methylenedioxy)-benzaldehyde and 124 g of 2,2,6,6-tetramethyl-4-aminopiperidine were reacted and worked up as in Example 28a. 154 g of the compound of the formula

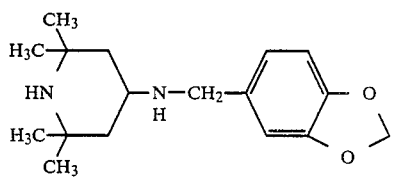

were obtained as a colorless liquid of boiling point 154°–155° C./0.1 mmHg.

Calculated: C 70.3 H 9.0 N 9.6 O 11.0%. Found: C 70.0 H 8.9 N 10.0 O 11.3%.

(b) 58 g of the product from (a) were reacted and worked up as in Example (14b). Recrystallization from acetonitrile gave 18 g of the compound of the formula

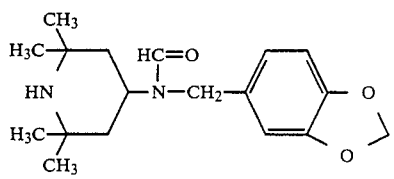

as a colorless solid of melting point 95° C.

Calculated: C 67.9 H 8.2 N 8.8 O 15.1%. Found: C 67.9 H 8.4 N 8.8 O 14.9%.

EXAMPLE 44

(a) 50 g of 2,4,6-trimethylbenzaldehyde and 53 g of 2,2,6,6-tetramethyl-4-aminopiperidine were reacted and worked up as in Example (28a). 74 g of the compound of the formula

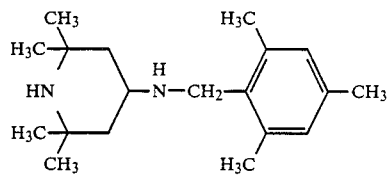

were obtained as a colorless oil of boiling point 150°–151° C./0.1 mmHg, which solidified to a colorless solid of melting point 53° C.

Calculated: C 79.1 H 11.2 N 9.7%. Found: C 78.6 H 11.2 N 9.8%.

(b) 51 g of the product from (a) were reacted and worked up as in Example (14b). After removal of the solvent, the residue was recrystallized from acetonitrile. 42 g of the compound of the formula

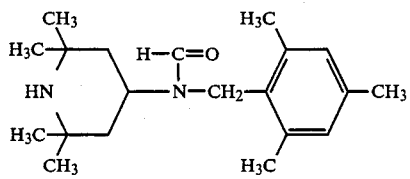

of melting point 133° C. were obtained.

Calculated: C 75.9 H 10.2 N 8.8 O 5.0%. Found: C 75.6 H 10.0 N 8.9 O 5.1%.

EXAMPLE 45

(a) 68.8 g of pivalaldehyde and 125 g of 2,2,6,6-tetramethyl-4-aminopiperidine were reacted and worked up as in Example (28a). 115 g of the compound of the formula

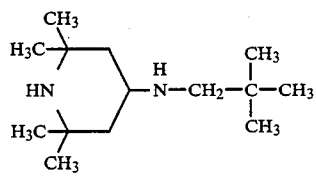

were obtained as a colorless liquid of boiling point 76°–77° C./0.3 mmHg.

Calculated: C 74.3 H 13.3 N 12.4%. Found: C 73.6 H 13.4 N 12.8%.

(b) 65 g of the product from (a) were reacted and worked up as in Example (14b). 52 g of the compound of the formula

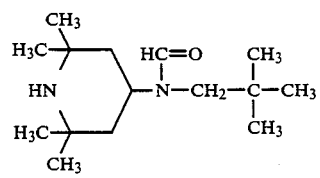

were obtained as a colorless oil of boiling point 116°–118° C./0.1 mmHg, which solidified to a colorless solid of melting point 64° C.

Calculated: C 70.8 H 11.9 N 11.0 O 6.3%. Found: C 70.5 H 11.9 N 11.0 O 6.7%.

EXAMPLE 46

(a) 70 g of cyclododecanone, 61 g of 2,2,6,6-tetramethyl-4-aminopiperidine and 5 g of p-toluenesulfonic acid monohydrate were reacted and worked up as in Example (25a). 88 g of the compound of the formula

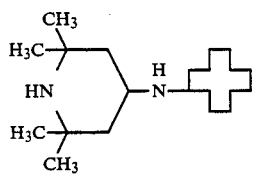

were obtained as a colorless liquid of boiling point 152°–154° C./0.15 mmHg.

Calculated: C 78.2 H 13.1 N 8.7. Found: C 78.0 H 13.1 N 8.8.

(b) 46 g of the product from (a) were reacted and worked up as in Example (14b). After removal of the solvent, the residue was recrystallized from acetonitrile. 34 g of the compound of the formula

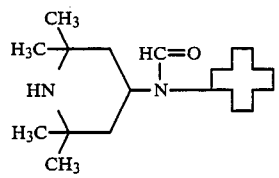

were obtained as a colorless solid of melting point 155° C.

Calculated: C 75.4 H 12.1 N 8.0 O 4.6%. Found: C 75.2 H 11.9 N 8.0 O 4.6%.

EXAMPLE 47

(a) 112 g of 4-chloro-1-butanol in 100 ml of acetonitrile were added dropwise to 145 g of 2,2,6,6-tetramethyl-4-aminopiperidine, 94 g of triethylamine and 1 g of potassium iodide in 150 ml of acetonitrile, and the mixture was stirred for 2 hours at room temperature and refluxed for 6.5 hours while stirring. The precipitate which separated out was filtered off under suction and dissolved in water and the solution was rendered alkaline with sodium hydroxide solution and extracted with n-butanol. After phase separation, the organic phase was freed from the solvent under reduced pressure from a water pump and the residue was distilled. 57 g of the compound of the formula

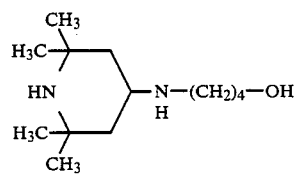

were obtained as a colorless liquid of boiling point 175°–177° C./12 mmHg, which solidified to a colorless solid of melting point 85° C.

Calculated: C 68.4 H 12.3 N 12.3 O 7.0%. Found: C 68.1 H 12.4 N 12.1 O 7.1%.

(b) 44.3 g of the product from (a) were reacted and worked up as in Example (12b). 19.3 g of a 1:1 mixture of the compounds of the formulae

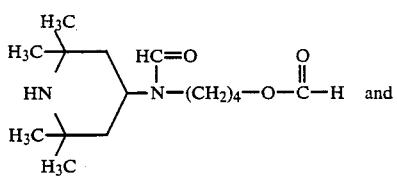

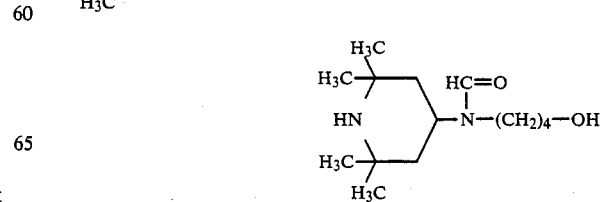

were obtained as a colorless liquid of boiling point 180° C./0.5 mmHg.

Calculated: C 64.4 H 10.4 N 10.4 O 14.8%. Found: C 64.6 H 10.6 N 10.5 O 14.4%.

EXAMPLE 48

(a) 260.4 g of 2-(4-morpholinyl)-ethylamine and 310 g of 2,2,6,6-tetramethyl-4-piperidone were reacted and worked up as in Example (10a). 50 g of the compound of the formula

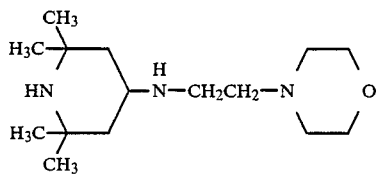

were obtained as a colorless liquid of boiling point 109°–111° C./0.3 mmHg.

Calculated: C 66.8 H 11.6 N 15.9 O 6.0%. Found: C 66.3 H 11.6 N 15.4 O 6.8%.

(b) 33 g of the product from (a) were reacted and worked up as in Example (14b). 29 g of the compound of the formula

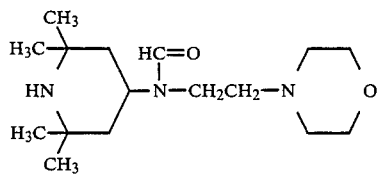

were obtained as a colorless liquid of boiling point 174°–176° C./0.5 mmHg, which solidified to a colorless solid of melting point 89° C.

Calculated: C 64.6 H 10.5 N 14.2 O 10.8%. Found: C 64.2 H 10.6 N 14.8 O 10.9%.

EXAMPLE 49

80 g of the product from Example 5 were introduced into 250 ml of acetic anhydride and the mixture was boiled for 3.5 hours. The reaction mixture was added dropwise to a mixture of 400 g of 50% strength sodium hydroxide solution and 400 g of ice. The precipitate which separated out was filtered off under suction, washed neutral with water, dried, and recrystallized from cyclohexane. 57 g of the compound of the formula

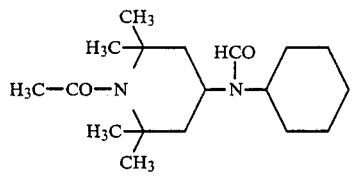

were obtained as a colorless solid of melting point 129° C.

Calculated: C 70.1 H 10.5 N 9.1 O 10.4%. Found: C 70.2 H 10.5 N 9.1 O 10.4%.

We claim:
1. A 4-formylaminopiperidine of the formula (I)

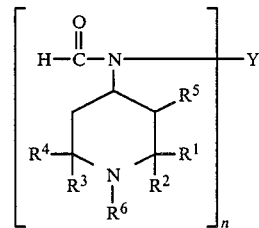

(II)

where n is 1 or 2, $R^1$, $R^2$, $R^3$ and $R^4$ independently of one another are each $C_1$–$C_4$-alkyl, or $R^1$ and $R^2$ or $R^3$ and $R^4$ together form a tetramethylene or pentamethylene group, $R^5$ is hydrogen or $C_1$–$C_4$-alkyl, $R^6$ is hydrogen, $C_1$–$C_{22}$-alkyl or $C_3$–$C_{22}$-alkenyl or is $C_7$–$C_{12}$-phenylalkyl which is unsubstituted or substituted by $C_1$–$C_4$-alkyl, $C_1$–$C_4$-alkoxy, fluorine, chlorine, methylenedioxy, ethylenedioxy or di-$C_1$–$C_4$-alkylamino or is $C_1$–$C_{22}$-alkanoyl, $C_2$- or $C_3$-cyanoalkyl, $C_1$–$C_{22}$-hydroxyalkyl or $C_2$–$C_{22}$-aminoalkyl and, when n is 1, y is hydrogen, $C_1$–$C_{22}$-alkyl, $C_3$–$C_{22}$-alkenyl, $C_3$–$C_{12}$-cycloalkyl or bicycloalkyl or is $C_2$–$C_{22}$-alkyl which is substituted by cyano, hydroxyl or carbo-$C_1$–$C_4$-alkoxy, or is $C_4$–$C_{22}$-alkyl which is interrupted by ether oxygen, nitrogen or sulfur, or is $C_7$–$C_{22}$-phenyl- or diphenylalkyl, $C_7$–$C_{22}$-phenylalkyl which is substituted by $C_1$–$C_4$-alkyl, $C_1$–$C_4$-alkoxy, fluorine, chlorine, methylenedioxy, ethylenedioxy or di-$C_1$–$C_4$-alkylamino, or is phenyl which is unsubstituted or substituted by $C_1$–$C_4$-alkyl or carbo-$C_1$–$C_4$-alkoxy, or is a radical of the formula

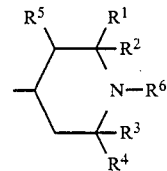

or

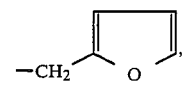

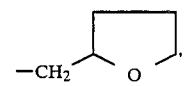

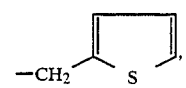

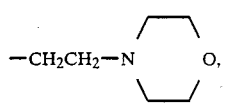

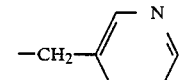

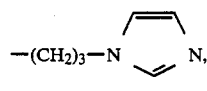

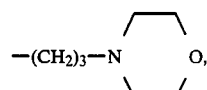

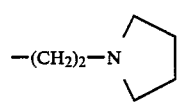

or

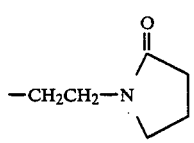

or, when n is 2, Y is $C_2$–$C_{22}$-alkylene, $C_5$–$C_{22}$-cycloalkylene, $C_8$–$C_{14}$-phenylalkylene or phenylene, or is $C_4$–$C_{30}$-alkylene which is interrupted by ether oxygen, nitrogen, sulfur or the acid addition salts of this compound.

2. The piperidine as claimed in claim 1, wherein, for group Y, said $C_1$–$C_{22}$-alkyl is methyl, ethyl, n-propyl, isopropyl, n-butyl, isobutyl, n-pentyl, isopentyl, hexyl, octyl, decyl, dodecyl, octadecyl, pivalyl, 3,3-di-methyl-but-2-yl, neopentyl, 4-methylpent-2-yl or 2-ethylhexyl.

3. The piperidine as claimed in claim 1, wherein, for group Y, said $C_3$–$C_{22}$-alkenyl is allyl, butenyl, pentenyl, or oleyl.

4. The piperidine as claimed in claim 1, wherein, for group Y, said $C_3$–$C_{12}$-cycloalkyl is cyclopropyl, cyclobutyl, cyclopentyl, cyclohexyl, methylcyclohexyl, cycloheptyl, cyclooctyl, cyclododecyl, or bicycloheptyl.

5. The piperidine as claimed in claim 1, wherein, for group Y, said substituted $C_2$–$C_{22}$-alkyl is cyanomethyl, hydroxyethyl, hydroxypropyl, hydroxybutyl, carbomethoxyethyl or carboethoxyethyl.

6. The piperidine as claimed in claim 1, wherein, for group Y, said $C_4$–$C_{22}$-alkyl interrupted by oxygen or nitrogen is —(CH$_2$)$_3$N(CH$_3$)$_2$, —(CH$_2$)$_3$N(C$_2$H$_5$)$_2$, —(CH$_2$)$_3$—OCH$_3$, —(CH$_2$)$_3$—O—CH(CH$_3$)$_2$, —(CH$_2$)$_2$O(CH$_2$)$_2$—OH, —CH$_2$—(CH$_2$)$_2$—CH$_2$—N(CH$_3$)$_3$, —(CH$_2$)$_2$—N[(CH(CH$_3$)$_2$]$_2$, —(CH$_2$)$_2$—N(C$_2$H$_5$)$_2$, —(CH$_2$)$_2$N(CH$_3$)$_2$, —(CH$_2$)$_2$OCH$_3$ or —(CH$_2$)$_2$OCH$_2$CH$_3$.

7. The piperidine as claimed in claim 1, wherein, for group Y, said unsubstituted or substituted $C_7$–$C_{22}$-phenyl- or diphenylalkyl is benzyl, methoxybenzyl, methylbenzyl, ethylbenzyl, isopropylbenzyl, trimethylbenzyl, fluorobenzyl, chlorobenzyl, methylenedioxybenzyl, phenylethyl, phenylpropyl, phenylbutyl, dimethylaminobenzyl, diphenylmethyl or 1,3-diphenyl-prop-2-yl.

8. The piperidine as claimed in claim 1, wherein, for group Y, said substituted phenyl is tolyl or carbo-$C_1$–$C_4$-alkoxy substituted phenyl.

9. The piperidine as claimed in claim 1, wherein, for group Y when n is 2, said $C_2$–$C_{22}$-alkenyl or $C_5$–$C_{22}$-cycloalkylene is —(CH$_2$)$_o$—CH$_2$, where 0 is from 1 to 21,

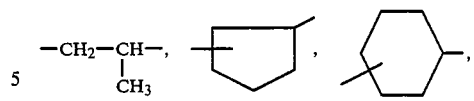

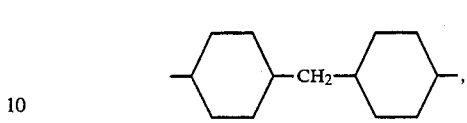

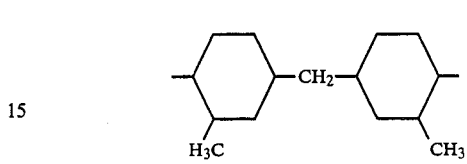

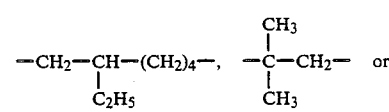

10. The piperidine as claimed in claim 1, wherein, for group Y when n is 2, said $C_8$–$C_{14}$-phenylalkylene or phenylene is

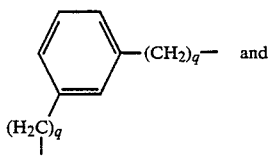

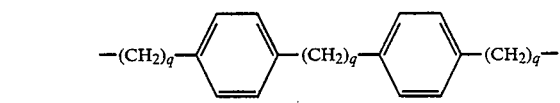

wherein q is 0–4.

11. The piperidine as claimed in claim 1, wherein, for group Y, when n is 2, said alkylene interrupted by oxygen, nitrogen or heterocyclic structures is —(CH$_2$)$_3$O(CH$_2$)$_4$O(CH$_2$)$_3$—, —(CH$_2$)$_3$O(CH$_2$)$_2$O(CH$_2$)$_2$O(CH$_2$)$_3$—,

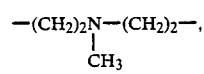

—(CH$_3$H$_6$O)$_r$—C$_3$H$_6$—where r is from 1 to 33,

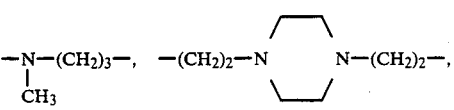

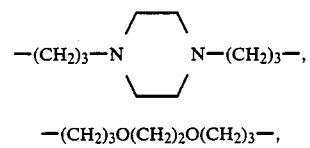

—(CH$_2$)$_3$O(CH$_2$)$_2$O(CH$_2$)$_3$—,

-continued

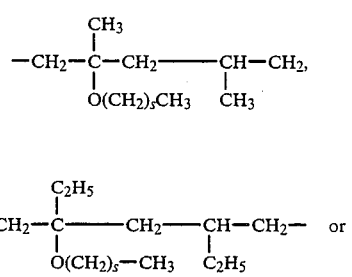

-continued

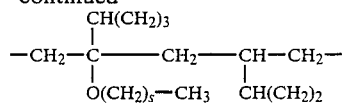

where s is from 0 to 7.

12. A piperidine as claimed in claim 1, wherein, in the formula, $R^1$, $R^2$, $R^3$ and $R^4$ are each methyl.

13. A piperidine as claimed in claim 1, wherein, in the formula, $R^5$ is hydrogen.

14. A piperidine as claimed in claim 2, wherein $R^5$ is hydrogen.

15. A stabilized organic material containing one or more piperidine derivatives as claimed in claim 1.

* * * * *